(12) United States Patent
Farahmand et al.

(10) Patent No.: US 10,610,129 B1
(45) Date of Patent: Apr. 7, 2020

(54) SYSTEMS AND METHODS FOR PORTABLE MONITORING OF INCENTIVE SPIROMETRY

(71) Applicant: FOAD FARAHMAND MD PLLC, Plano, TX (US)

(72) Inventors: Farid Farahmand, Plano, TX (US); Foad Farahmand, Plano, TX (US)

(73) Assignee: FOAD FARAHMAND MD PLLC, Plano, TX (US)

( * ) Notice: Subject to any disclaimer, the term of this patent is extended or adjusted under 35 U.S.C. 154(b) by 0 days.

(21) Appl. No.: 16/174,903

(22) Filed: Oct. 30, 2018

(51) Int. Cl.
*A61B 5/091* (2006.01)
*A61B 5/08* (2006.01)
*A61B 5/00* (2006.01)

(52) U.S. Cl.
CPC ............ *A61B 5/091* (2013.01); *A61B 5/0803* (2013.01); *A61B 5/486* (2013.01); *A61B 5/7425* (2013.01); *A61B 5/7475* (2013.01)

(58) Field of Classification Search
CPC ..... A61B 5/0022; A61B 5/0803; A61B 5/087; A61B 5/0871; A61B 5/091; A61B 5/097; A61B 5/486; A61B 5/7425; A61B 5/7475
See application file for complete search history.

(56) References Cited

U.S. PATENT DOCUMENTS

| | | | | |
|---|---|---|---|---|
| 5,522,380 A * | 6/1996 | Dwork | .............. | A61M 15/0086 128/200.23 |
| 6,238,353 B1 * | 5/2001 | Weinstein | ............ | A61B 5/0875 600/538 |
| 9,138,167 B1 * | 9/2015 | Leydon | .................. | A61B 5/087 |
| 2011/0247620 A1 * | 10/2011 | Armstrong | ........... | B01D 53/047 128/204.23 |
| 2011/0247621 A1 * | 10/2011 | Richard | .............. | B01D 53/047 128/204.23 |
| 2011/0247622 A1 * | 10/2011 | Schneider | ............ | B01D 53/047 128/204.23 |
| 2012/0000462 A1 * | 1/2012 | Edwards | .............. | B01D 53/047 128/201.21 |
| 2013/0066225 A1 * | 3/2013 | Kojouri | .................. | A61B 5/087 600/538 |
| 2013/0204151 A1 * | 8/2013 | Amirkhanian | ....... | A61B 5/0875 600/538 |
| 2015/0363566 A1 * | 12/2015 | Johnson | .............. | G06F 19/3481 705/3 |
| 2016/0106375 A1 * | 4/2016 | Leydon | .................. | A61B 5/087 600/538 |
| 2017/0000382 A1 * | 1/2017 | Leydon | ............... | A61M 15/009 |
| 2017/0119279 A1 * | 5/2017 | Ahmad | .................... | A61B 5/74 |

(Continued)

*Primary Examiner* — Orlando Bousono
(74) *Attorney, Agent, or Firm* — Sheppard, Mullin, Richter & Hampton LLP

(57) ABSTRACT

A portable incentive spirometry monitoring device and method of use. The device connected to the base of an incentive spirometer and is capable of monitoring inspiration within the incentive spirometer. The portable incentive spirometry monitoring device has a user interface for inputting a variety of different parameters, including a desired air volume, as well as attempt thresholds. Results can be stored such that medical personnel can review attempts by a patient to monitor therapeutic use, as well as encouraging patient use. The portable incentive spirometry monitoring device may be reused with different incentive spirometers without the need for extensive sterilization.

8 Claims, 6 Drawing Sheets

(56) References Cited

U.S. PATENT DOCUMENTS

| | | | |
|---|---|---|---|
| 2017/0119280 A1* | 5/2017 | Ahmad | A61B 5/74 |
| 2017/0182267 A1* | 6/2017 | Cameron | A61M 11/042 |
| 2017/0224251 A1* | 8/2017 | Ahmad | A61B 5/74 |
| 2017/0273597 A1* | 9/2017 | Schuelke | A61B 5/087 |
| 2018/0000379 A1* | 1/2018 | Eltorai | A61B 5/091 |
| 2018/0064402 A1* | 3/2018 | Leydon | A61B 5/0026 |
| 2018/0263528 A1* | 9/2018 | Leydon | A61M 15/0021 |
| 2018/0330827 A1* | 11/2018 | Johnson | G06F 19/3481 |

* cited by examiner

SYSTEMS AND METHODS FOR PORTABLE MONITORING OF INCENTIVE SPIROMETRY

TECHNICAL FIELD

The present disclosure relates generally to systems and methods to monitor incentive spirometry. More particularly, the technology is directed to a portable monitoring device configured to monitor use of an incentive spirometer and providing local feedback.

DESCRIPTION OF THE RELATED ART

Postoperative pulmonary complications, including atelectasis, pneumonia, and respiratory failure, commonly arise in patients following major cardiac, thoracic, and abdominal surgeries. Deep breathing exercises help reduce postoperative pulmonary complications by improving postoperative lung expansion and ventilation. Incentive spirometry, designed to mimic natural yawning or sighing, is routinely prescribed by clinicians as a therapeutic strategy to encourage deep breathing. Incentive spirometry forces the patient to take long, deep breaths, which decreases plural pressure and increases lung expansion and gas exchange. Incentive spirometry is accomplished through use of an incentive spirometer, a device that provides feedback when a patient inhales at a predetermined volume for a minimum of five seconds. Inhalation results in the raising of a piston within the device, and a successful attempt is achieved when the piston raises to a set target volume.

BRIEF SUMMARY OF THE DISCLOSURE

Embodiments described herein are directed to systems and methods for monitoring incentive spirometry through a portable device.

In one embodiment, a method of monitoring incentive spirometry through a portable device includes: receiving a desired air volume through a user interface; sensing an inspired air volume in an incentive spirometer operationally connected to the portable device; determining whether the inspired air volume exceeds or is equal to the desired air volume; and displaying through a visual indication at the portable device, whether the inspired air volume exceeds or is equal to the desired air volume.

In embodiments, the desired air volume is based on a plurality of measurements including height, sex, age, and weight. In some embodiments, sensing the inspired air volume comprises tracking displacement of a piston within the incentive spirometer. In some embodiments, sensing the inspired air volume comprises tracking displacement of a piston within the incentive spirometer over a defined period of time (e.g., years, months, weeks, days, hours, minutes, seconds, etc.).

In some embodiments, recording of an attempt may start when an attempt threshold is reached.

In one embodiment, a method for monitoring incentive spirometer compliance includes: receiving a desired air volume through a user interface; sensing an inspired air volume in an incentive spirometer operationally connected to the portable device during a period of time; determining whether the inspired air volume exceeds or is equal to the desired air volume during the period of time; incrementing a counter each time the inspired air volume exceeds or is equal to the desired air volume during the period of time; summating a plurality of increments during the period of time; and displaying, through a visual indication at the portable device, an output summation of the plurality of increments during the period of time.

In embodiments, the desired air volume is based on a plurality of measurements comprising at least one of sex, height, age, and weight, among other measurements. In some embodiments, sensing the inspired air volume comprises tracking displacement of a piston within the incentive spirometer. In some embodiments, the visual indication displays a plurality of parameters including attempts, successes, a goal, elapsed time, maximum volume, and minimum volume. In some embodiments, an attempt is recorded when an attempt threshold is reached.

In one embodiment, a device for monitoring incentive spirometry comprises: a user interface through which a desired air volume is input; a sensor measuring inspired air volume in an incentive spirometer operationally connected to the portable device by tracking displacement of a piston within the incentive spirometer; a processor incrementing a counter each time the piston has been displaced up to or exceeding the desired air volume; and a display presenting a visual indication of the number of times the piston has been displaced up to or exceeding the desired air volume.

In embodiments, the user interface comprises a plurality of switches, where a switch may increment or decrement the desired air volume. In some embodiments, the sensor measures an inspired air volume by tracking time a time of flight of the piston through a light signal. In some embodiments, the sensor measures the inspired air volume by tracking the time of flight of a piston through a sound signal.

In embodiments, the display presents a plurality of parameters including at least one of an attempt, a success, a goal, an elapsed time, a maximum volume, and a minimum volume. In some embodiments, the display is a LCD screen. In some embodiments, the display is a plurality of LEDs. Audible indicators, such as a buzzer, may be included in various embodiments. In some embodiments, the portable device is operationally attached to the incentive spirometer. In some embodiments, the portable device is operationally detached from the incentive spirometer.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present disclosure, in accordance with one or more various embodiments, is described in detail with reference to the following figures. The drawings are provided for purposes of illustration only, and merely depict typical or example embodiments. These drawings are provided to facilitate the reader's understanding of various embodiments and shall not be considered limiting of the breadth, scope, or applicability of the present disclosure. It should be noted that for clarity and ease of illustration these drawings are not necessarily made to scale.

The figures are not exhaustive and do not limit the present disclosure to the precise form disclosed.

DETAILED DESCRIPTION

Embodiments of the present disclosure are directed to systems and methods for monitoring incentive spirometry through a portable device to facilitate self-administration and patient participation. Incentive spirometry is designed to expand lung capacity by forcing a user to breath sustained deep breaths. Use of an incentive spirometer is often prescribed by medical personnel following surgery to prevent post-operative complications, as well as for many respiratory diseases (e.g., pneumonia). As used herein, the term "incentive spirometry" refers to spirometry performed by an individual using an incentive spirometer.

The effectiveness of incentive spirometry for the prevention of postoperative pulmonary complications, or for hindering the progression of many respiratory diseases, is dependent on thorough provider instruction and sustained patient participation. Providers agree that best results are obtained when the device is used consistently. Insufficient self-administration can prevent the resolution of complications leading to prolonged hospital stays, high readmission rates (that are not reimbursed by insurance or hospital), and increased healthcare costs. Incentive spirometers with visual and auditory markers were introduced recently to encourage patient participation, but have had little effect. Furthermore, as hospital admissions increase, medical personnel have less time to spend with each patient to monitor regular incentive spirometer use. Accordingly, there is a need in the art for a device capable of tracking patient incentive spirometer use and providing feedback that encourages further use. The systems and methods disclosed herein provide a way to meet this need by efficiently tracking user compliance, and by notifying medical personnel of that achievement.

Embodiments of the technology discussed herein provide a mechanism for efficiently tracking user compliance, and notifying medical personnel of that compliance. User compliance may be monitored by a portable monitoring device that tracks the inspired air volume by a user, processes that information by comparing it to a desired air volume inputted by medical personnel, and displays a visual indication of results of the comparison. The term "medical personnel" as used herein includes nurses, doctors, physician assistants, researchers, or other persons monitoring incentive spirometry.

Figure 1:
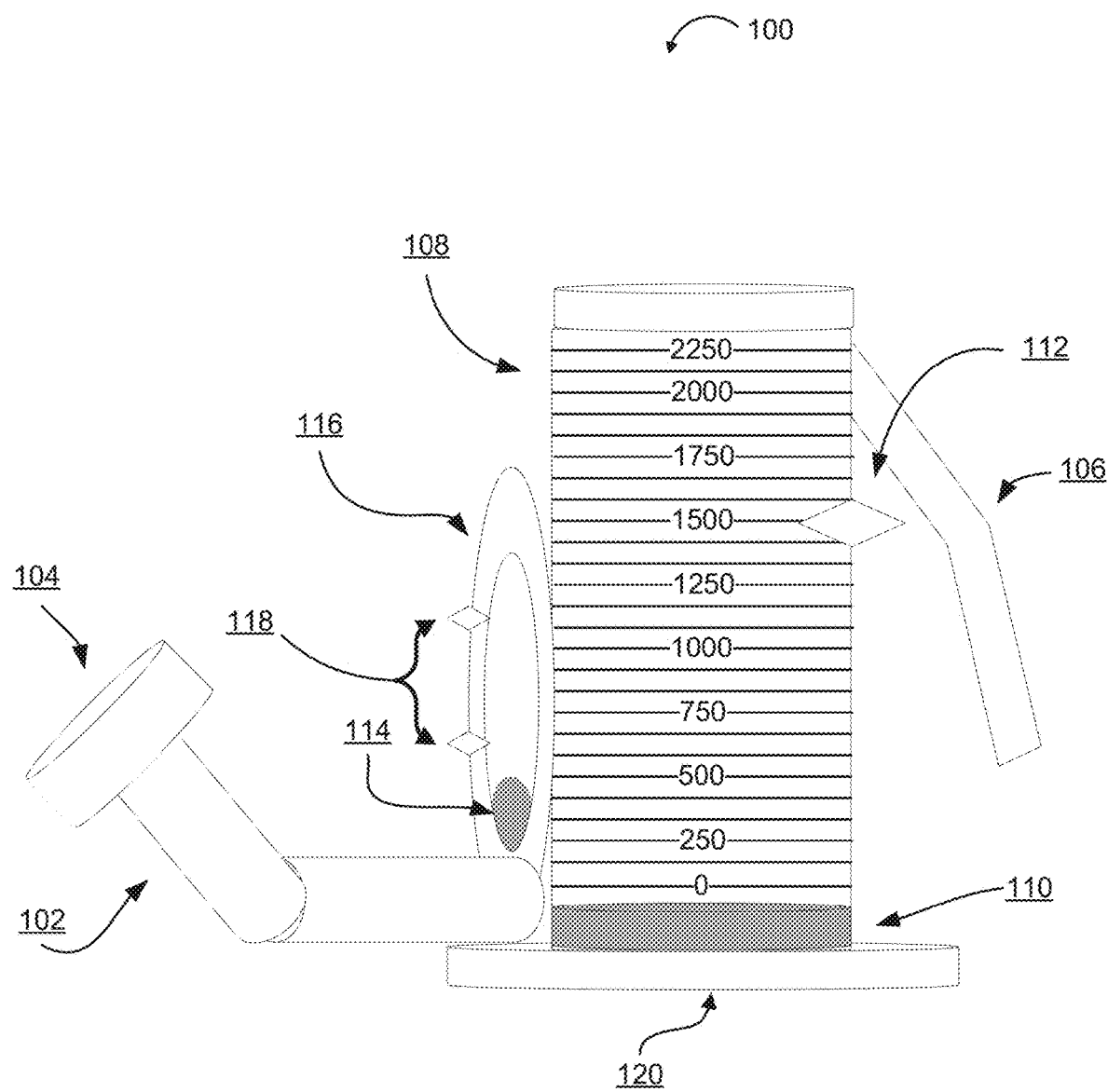
FIG. 1 illustrates an example incentive spirometer.

FIG. 1 depicts an example incentive spirometer 100 within the prior art. The technology disclosed herein enables greater functionality for medical professionals and users. As illustrated, incentive spirometer 100 may include, for example, an inhalation tube 102 with a mouthpiece 104, a handle 106, a base 120, an air chamber 108, a piston 110 within the air chamber 108, an adjustable marker 112, an indicator 114 inside a separate chamber 116 to indicate whether the user is inhaling too rapidly, and a base 120.

When a user inspires through the inhalation tube 102 (via the mouthpiece 104 in the illustrated example), the piston 110 within the air chamber 108 rises, indicating a volume of air the inspired. The volume of air inspired, as used herein, is the total volume of air inhaled into (or exhaled from) the lungs during a single breath. The adjustable marker 112 may be positioned to indicate, for example, the volume of air the user should reach/attain through inspiration when using the device. The adjustable marker 112 may also indicate, for example, the maximum volume of air achieved by the user through inspiration. The separate chamber 116 located next to the air chamber 108 identifies to the user whether he or she is inhaling too quickly by moving the indicator 114 housed within the separate chamber 116 upwards or downwards. Markers 118 located on the outside of the separate chamber 116 provide guidance to the user, so that the he or she may inspire at a constant or otherwise desired rate.

Figure 2A:
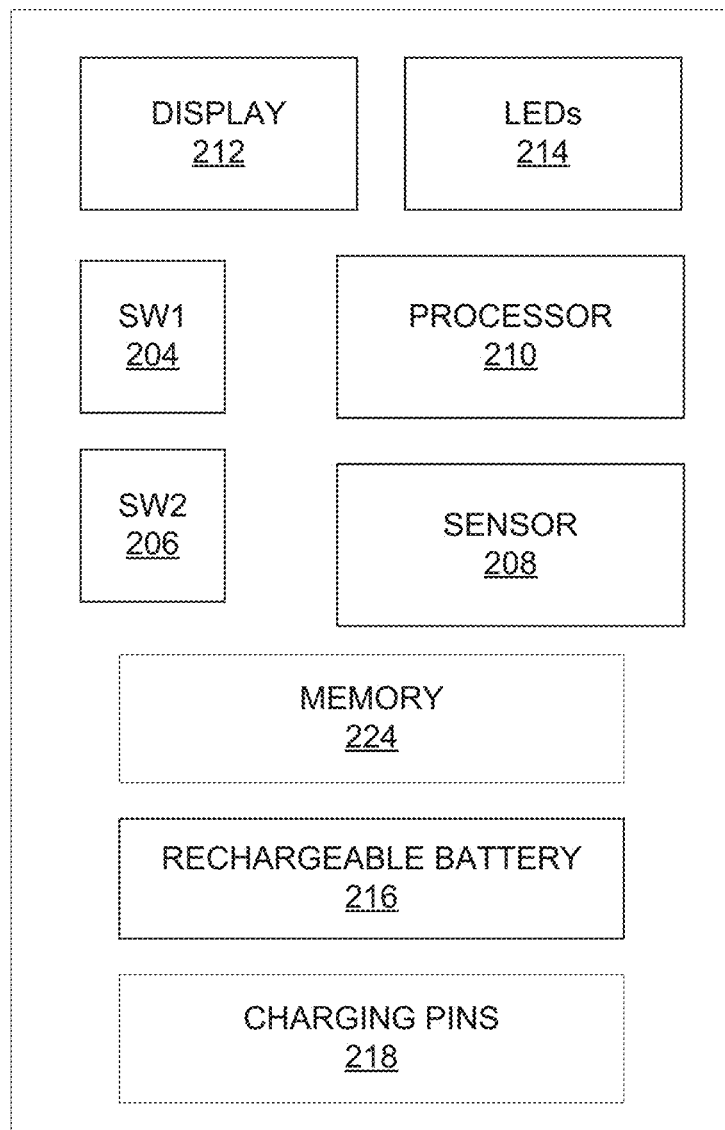
FIG. 2A illustrates an example environment in which embodiments of the disclosure may be implemented.
Figure 2A:
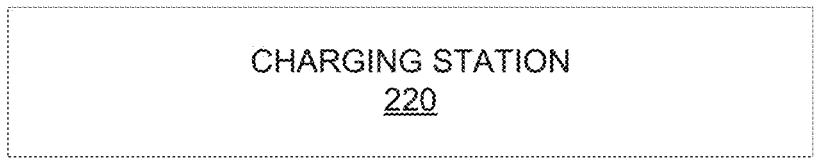

FIG. 2A is a block diagram illustrating an example portable monitoring device 200 in accordance with the technology disclosed herein. The portable monitoring device 200 enables medical professionals to ensure patient compliance using the incentive spirometer 100 at the device itself, eliminating the need for the communication of raw data to a networked system for determination. As illustrated, the portable monitoring device 200 in various embodiments may include a first switch 204, a second switch 206, a sensor 208, a processor 210, an display 212, a plurality of LEDs 214, a rechargeable battery 216, charging pins 218, and a charging station 220 to which the portable monitoring device 200 may be connected.

The first switch 204 and second switch 206 may be operatively connected to a processor 210. The first switch 204 and second switch 206 may comprise buttons, toggles, or any other components capable of receiving input (e.g., tactile input) from a user. In various embodiments, the first switch 204 and second switch 206 may be used by medical personnel to input, for example, a desired air volume based on the user. As used herein, the term "desired air volume" (or predicted goal, or goal) means a standardized air volume based on the individual user's sex, weight, height, age, and/or other parameters specific to that individual user (e.g., past surgeries, smoking history, workout history, diabetes, history of cancer, other illnesses, etc.). In various embodiments, the desired air volume may be an air volume between the range of about 250 mL to about 3000 mL. The desired air volume could be represented as a range of volumes (for example, between about 450 mL and 475 mL) or discrete volume with some tolerance for variation in achieving the desire air volume (for example, about 550 mL).

In various embodiments, medical personnel can use the first switch 204 to increment the desired air volume, and the second switch 206 allows a medical personnel to decrement the desired air volume. In embodiments, the first switch 204 and second switch 206 may increment or decrement the desired air volume by a range between about 1 mL to about 1000 mL, or from about 200 mL to about 2000 mL. In various embodiments, the desired air volume may be incremented or decremented by a range between about 250 mL to about 500 mL.

The amount of change caused by incrementing or decrementing may vary between embodiments, depending on the level of precision required. For example, the desired air volume may be incremented by 50 mL at a time in some embodiments, or 1 mL at a time in other embodiments. A person of ordinary skill in the art would know how to vary the amount of increase or decrease based on the needs of a particular implementation, and the examples provided should not be interpreted as limiting the subject matter of this disclosure to any particular amount of variation in the increment or decrement.

The first switch 204 and the second switch 206 may be pressed at the same time in some embodiments to reset the desired air volume. Pressing the first switch 204 and the second switch 206 simultaneously in such situations begins a command function to reset the desired air volume. Pressing the first switch 204 and the second switch 206 simultaneously sends a signal to the processor 210, which is operatively connected to the first switch 204 and second switch 206, to initiate a command whereby the processor 210 sends a signal to the LEDs 214, which are operatively connected to the processor 210. Once the command is received by the LEDs 214, the LEDs 214 will begin blinking and the desired air volume may then be inputted. If the LEDs 214 do not blink, the first switch 204 and second switch 206 may be simultaneously pressed again to resend the command. In embodiments, once the desired air volume is set, the first switch 204 and the second switch 206 may then be pressed and held simultaneously to set the new desired air volume.

In embodiments, the first switch 204 and second switch 206 may be pressed simultaneously to reset the elapsed time. The reset of elapsed time in this manner may occur simultaneously with resetting the desired air volume as discussed above, while other embodiments may have the first time the switches are pressed at the same time reset the desired air volume and a second time the switches are pressed at the same time resets the elapsed time. In other embodiments, a time reset switch (not pictured) may be included to reset the elapsed time.

The switches 204, 206 may be configured to perform a variety of functions of the portable monitoring device 200, some of which are discussed above. In various embodiments, the switches 204, 206 may be configured, individually or in combination, to perform one or more of the following functions: increment/decrement desired air volume; set the minimum desired air volume; set one or more thresholds; control the display 212; initiate a transfer of data from the portable monitoring device 200 to a remote location; among others. In various embodiments, additional switches may also be included in addition to the first switch 204 and second switch 206.

In various embodiments, the actions of switches 204, 206 may vary depending on the function to be performed. For example, in some embodiments one or more switches may be configured to increment a value when pressed, while holding the same switch may activate the configuration of thresholds. Non-limiting examples of the types of actions which the switches 204, 206 may perform include pushing, holding, toggling, twisting, among other depending on the type of switch implemented. In some embodiments, the switches 204, 206 may be different types of switches. For example, in some embodiments first switch 204 may be a toggle, capable of being flipped into one of two positions, while the second switch 206 is a rocker switch capable of being depressed in one or two directions continuously, returning to a neutral position after ever action. As another example, the first switch 204 may be a pushbutton, the second switch 206 a toggle, and a third switch (not pictured) is a rotary or dial. The type of switch may indicate the type of function a switch is capable of performing. A person of ordinary skill in the art would understand the capabilities of different switches and would know what type of switch to implement to perform the various functions of the portable monitoring device 200 discussed above. It should be noted that the use of alternatives to physical switches are contemplated. That is, the functionality one or more of the switches described herein, e.g., switches 204, 206, can be embodied using other mechanisms, for example, such as voice-activated switches/mechanisms that can perform the aforementioned incrementing, decrementing, etc. vis-à-vis audio input.

Although examples of the functions of the first switch 204 and second switch 206 have been discussed with specific reference to each respective switch, a person of ordinary skill in the art would understand that the modifiers "first" and "second" do not connote any priority in positioning on the portable monitoring device 200, or in position relative to each other.

Referring still to FIG. 2A, the portable monitoring device 200 includes one or more sensors 208. The sensors 208 are operatively connected to the processor 210. In various embodiments, the sensors 208 may measure the inspired air volume in the incentive spirometer 100 when the portable monitoring device 200 is connected to the incentive spirometer 100. In various embodiments, the sensors 208 measure inspired air volume by tracking the time of flight of the piston 110 within the air chamber 108 of the incentive spirometer 100, when the portable monitoring device 200 is connected to the incentive spirometer 100. The sensors 208 may track the time of flight through, for example, a light signal, including light signals transmitted from ambient, infrared, laser, or other light emitting sources. The sensors 208 may also track time of flight through, for example, a sound signal. Once the inspired air volume has been received by the sensors 208, the volumetric measurement of air may then be relayed to the processor 210. It is to be appreciated that the sensors 208 may track a plurality of time of flight measurements.

The sensors 208 may further include sensors for detecting a velocity at which air is inputted (i.e. through inhalation/inspiration) into the incentive spirometer 100. In various embodiments, the sensors 208 may include sensors for detecting an acceleration of the piston within the incentive spirometer 100.

The portable monitoring device 200 may also include a processor 210. The processor 210 may include circuits, such as logic or other circuits for one or more of receiving, processing, and/or storing content, data, or other information. The circuits may facilitate the receipt (e.g., as data input) of such content, data, or other information, as well as the generation of such content, data, or other information by the portable monitoring device 200. The circuits may further facilitate the transmission or delivery of such content, data or other information by the portable monitoring device 200. In embodiments, the processor 210 may receive the desired air volume from the first switch 204 and second switch 206, and may also receive detected data form the sensors 208. In various embodiments, the processor 210 receives a plurality of time of flight measurements from the sensors 208. In embodiments, the processor 210 converts the time of flight measurement into an inspired air volume. In embodiments, the processor 210 converts a plurality of time of flight measurements into inspired air volumes. The processor 210 may also receive other types of sensed data, such as the velocity of air input into the incentive spirometer and the period in which air was inputted into the incentive spirometer. The processor 210 can include logic to analyze the data received from the first switch 204, the second switch 206, the sensors 208, and other components of the portable monitoring device 200 to calculate various metrics, including but not limited to: number of attempts; whether a patient succeeded per the parameters; compliance; maximum inspired air volume (i.e., max volume); minimum inspired air volume (i.e., min volume); acceleration of the piston; total time air input was within recommended levels; percentage of time spent within the acceptable ranges for a success; among others. As described herein, an "attempt" is registered when the piston 110 reaches a certain threshold in the air chamber 108. For example, the threshold may be entered as 250 mL; if the piston 110 reaches or exceeds 250 mL in the air chamber 108, an attempt is registered. As described herein, "success" is registered when piston 110 in the air chamber 108 reaches (i.e., equals) or exceeds the threshold and desired air volume input by medical personnel. As used herein, "compliance" is the summation of successes over a period of time (t).

As described herein, the terms "maximum inspired air volume," or "max volume," refer to a volume of air associated with the highest point that piston 108 reaches. In various embodiments, max volume may be tracked over a period of time. For example, the highest point that piston 108 reaches over a period of, for example, 5 minutes, is the max volume. As described herein, the terms "minimum inspired air volume," or "min volume," refer to the volume of air associated with the lowest point that piston 108 reaches. In various embodiments, min volume may be tracked over a period of time. In various embodiments, the processor 210 may present a visual output of the processed inspired air volume(s), as well as other processed information (e.g., the desired air volume) through the LEDs 214 and/or display 212.

Portable monitoring device 200 may further include a memory 224 for storing thresholds, desired air volumes, inspired air volumes, and various different measurements. In various embodiments, the memory 224 may be a fixed or removable storage medium, such as, for example, a hard disk drive, a solid state drive, a magnetic tape drive, an optical disk drive, a compact disc (CD) or digital video disc (DVD) drive, flash memory, USB memory, or other form of fixed or removable storage medium. The type of storage medium may be dictated on the particular implementation, based on performance and/or form factor requirements that a person of ordinary skill in the art would understand and know how to select the storage medium that is appropriate. In various embodiments, the memory 224 may be computer-readable medium having stored therein computer software or data for performing the various functions of the portable monitoring device 200.

In embodiments, the portable monitoring device 200 such as the one depicted in FIG. 2A may include a display 212. Non-limiting examples of display 212 include: a liquid-crystal display (LCD); an organic LCD (OLCD); a light emitting diode display (LED); an organic light emitting diode display (OLED); digital light processing display (DLP); among others. The display 212 is operatively connected to the processor 210, and receives a information from the processor 210 that may be displayed to the user. Such information may include one or more of the following: desired air volume(s), inspired air volume(s) (e.g., attempts, successes, compliance, maximum inspired air volume, and minimum inspired air volume); time elapsed (in units of hours, minutes, seconds, etc.); or other information that may be useful to the user or medical personnel (e.g., flow rate).

In various embodiments, a user or medical personnel may interact with the display 212 screen. By way of example, such an display 212 may be a touchscreen that accepts various hand gestures as inputs.

As further depicted in FIG. 2A, embodiments of the portable monitoring device 200 may include a plurality of LEDs 214 (i.e., light emitting diode). The LEDs 214 are operatively connected to the processor 210, and receive information from the processor 210 that may be displayed to the user and medical personnel. The LEDs 214 may be any one or more of the following colors: red, green, blue, yellow, purple, white, black, and brown, or any combination thereof of RGB. Let it be appreciated that the list is not meant to be exhaustive, and more colors than the ones mentioned may be used. In various embodiments, the LEDs 214 are colored differently, where a color signifies certain information to the user and medical personnel. For example, in embodiments, the portable monitoring device may include two differently colored LEDs 214. One of the LEDs 214 may be, for example, a red LED and may signify to the user and medical personnel that the desired air volume input has not been achieved, while the other LED may be, for example, a green LED and may signify to the user and medical personnel that the desired air volume has been met. In embodiments, different combinations of colors may be used to signify different achievements.

In various embodiments, the LEDs 214 may be configured to indicate whether a patient has continued to comply with a recommended use over time. For example, an LED 214 may remain green during the period where the patient has been using the incentive spirometer 100 as required, but turn another color if the patient fails to use the incentive spirometer as many times as necessary. In this way, medical personnel can see whether a patient is using the incentive spirometer as scheduled, regardless of whether the patient has achieved the desired levels of performance.

The information represented by LEDs 214 discussed above could also be displayed on the display 212 in various embodiments.

Embodiments of the portable monitoring device may also include a rechargeable battery 216. The rechargeable battery 216 is operatively connected by circuitry to one or more components of the portable monitoring device 200 for supplying electric power. In embodiments, the rechargeable battery 216 is recharged when operatively connected to the charging station 220. Charging pins 218 located on one face of the portable monitoring device 202 interact with the charging station 220 to receive the electrical current. The rechargeable battery 216 may be consisted of any one of the following types: nickel cadmium, nickel-metal hybrid, lead acid, lithium ion, or lithium polymer.

The portable monitoring device 200 or components/features thereof may be implemented in combination with, or as an alternative to, other devices/features/components described herein, such as those described with reference to other embodiments and figures. The portable monitoring device 200 may additionally be utilized in any of the methods for making and/or using such devices/components/features described herein. The portable monitoring device 200 may also be used in various applications and/or permutations, which may or may not be noted in the illustrative embodiments described herein.

Figure 2B:
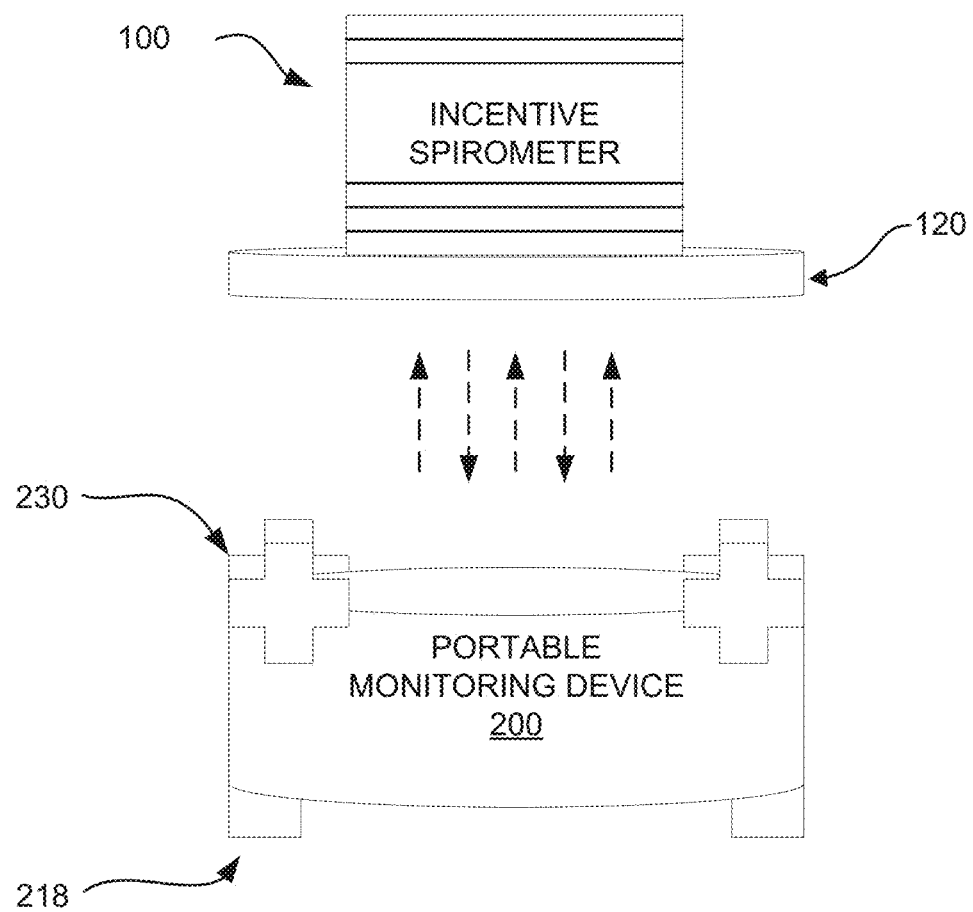
FIG. 2B illustrates an example portable monitoring device according to embodiments of the disclosure.

As illustrated in FIG. 2B, the portable monitoring device 200 may be operationally attached to the base 120 of an incentive spirometer 100. The portable monitoring device 200 has a top end, and a bottom end, and has a face capable a displaying through a visual indication, a plurality of user information. In embodiments, one face of the portable monitoring device 200 has charging pins 218 for charging the device. In other embodiments, one or more charging ports (not pictured) may be included to charge the portable monitoring device 200.

As illustrated, portable monitoring device 200 may include connecters 230 that are configured to mate with the base 120 of the incentive spirometer 100. The top of the portable monitoring device 200 may be cylindrical in shape, or may be round, square, rectangular, or a combination thereof. The connectors 230 may be mechanical and may include, for example, screws, latches, Velcro, locks, snaps, buttons, magnets, or some combination thereof. In various embodiments, the connectors 230 may be adjustable components, allowing the portable monitoring device 200 to mate with various different incentive spirometers that may have different shaped bases. The connectors 230 may comprise any suitable component for connecting to a generic incentive spirometer. For example, in some embodiments the connectors 230 may be elbow-like latches comprising an arm configured to clamp onto the base 120 and apply pressure in a downward direction to secure the base 120 to the top of the portable monitoring device 200. As another example, the connectors 230 may comprise component pairs configured to secure the base 120 of the incentive spirometer 100 to the top of the portable monitoring device 200, such as a strap and locking mechanism. A person of ordinary skill in the art would understand that a variety of different mechanisms may be used as connectors 230 and that the examples above are not meant to be limiting.

By utilizing a portable monitoring device 200 in accordance with the technology disclosed herein, medical personnel are capable of obtaining results indicative of a patient's progress at the incentive spirometer, without the need to transfer the data to another location. Moreover, medical personnel have greater flexibility in administering therapy through greater control over setting parameters and ensuring patient participation. The ability of connectors 230 to mate with a variety of different bases provides medical personnel with a single tool that can be attached to augment any type of incentive spirometer on hand. This lowers cost by facilitating the collection of relevant data for medical personnel regardless of the incentive spirometer used by the patient.

Further, unlike current approaches to monitoring incentive spirometry, the technology disclosed herein is less complex, allowing medical personnel to more reliably and efficiently ensure compliance by patients with recommended therapy. Current approaches require connection to a laptop or other computer system, complex setups and equipment, and require patients to come to the office. The embodiments of the technology of this disclosure are capable of conducting the required analysis locally at the incentive spirometer without the need for separate equipment, resulting in a less complex system that is smaller and more portable. This makes it easier for medical personnel and patients to view the incentive spirometer data at the device, eliminating the need to utilize other equipment. In some embodiments, the portable monitoring device may include a built in USB connector, enabling the portable monitoring device to be directly attached to a computer after use to store or review data, or (as discussed above) to charge the portable monitoring device.

Moreover, the technology of the present disclosure can be taken home by the patient, facilitating better compliance by eliminating the need to go somewhere else to perform the spirometry. Embodiments of the technology may store monitoring data performed at the patient's home or other non-medical personnel environment, which can then be reviewed by the medical personnel at the next meeting. The patient has the capability to reset, reconfigure, and setup the portable monitoring device at home himself or herself, enabling multiple measurements to be taken and maintained together for review later.

Embodiments of the technology disclosed herein further reduce the need for extensive sterilization techniques. Prior art monitoring solutions allowing for capturing and storing information associated with spirometry require time consuming and/or intensive cleaning and sterilization techniques to enable reuse between patients. Sterilization is required because these prior art solutions are more integrated with the incentive spirometer. Monitoring devices in accordance with the technology disclosed herein, however, reduce the need for such sterilization. The embodiments disclosed are compatible with cheaper, one-patient use incentive spirometers (that are not intended for reuse with another patient and, therefore, no need to sterilize). In this way, the monitoring device can be used in a fast and efficient manner with multiple patients without the need for extensive sterilization techniques. For example, after use with one patient, a monitoring device in accordance with the present disclosure can be removed from the first incentive spirometer, cleaned with a disinfectant wipe, and coupled to a second incentive spirometer for a second patient.

Figure 3:
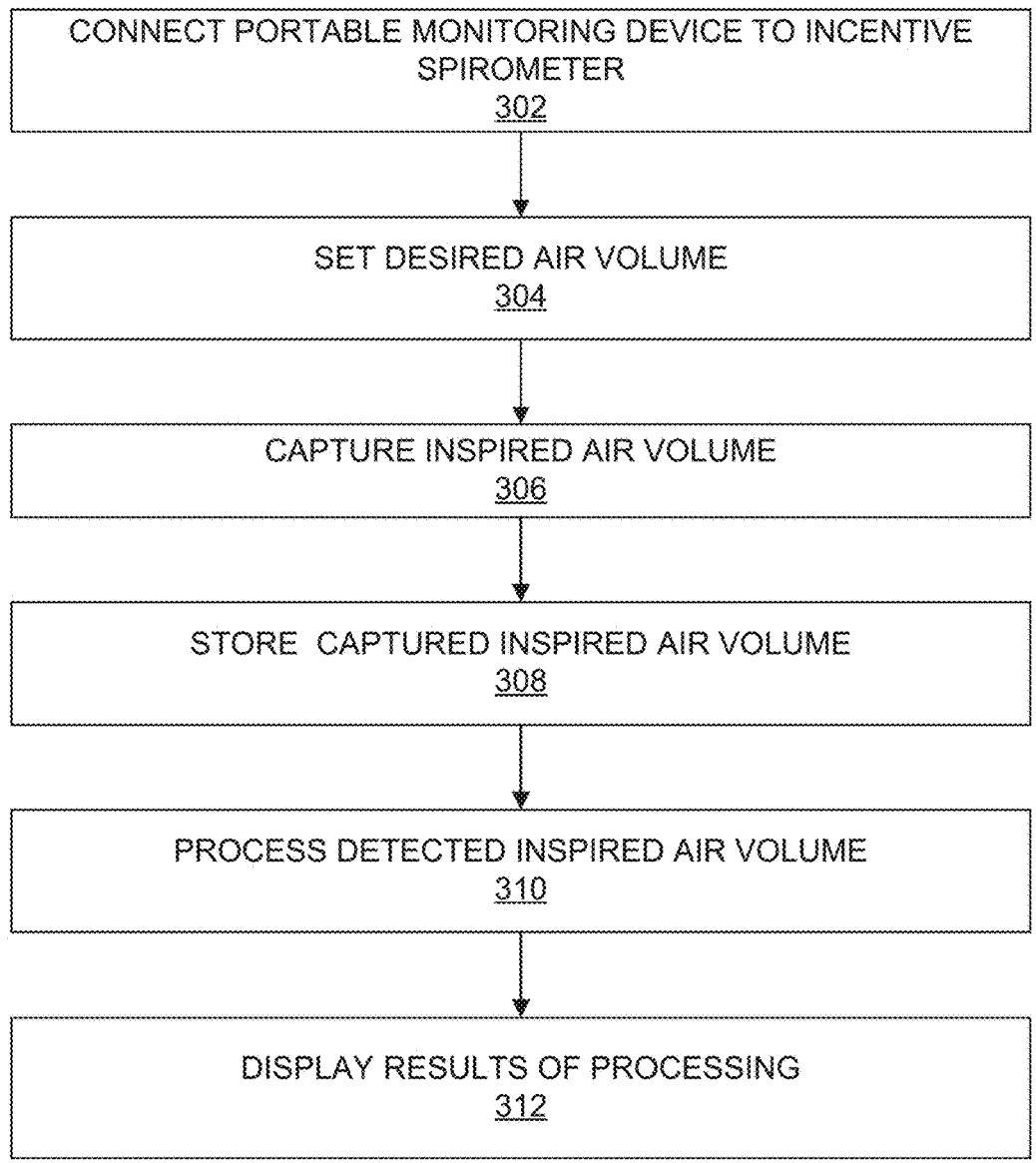
FIG. 3 is an operational flow diagram illustrating various operations that may be performed in accordance with embodiments of the disclosure.

FIG. 3 is a flow diagram illustrating an example method in accordance with the technology disclosed. At a high level, method 300 may be performed to monitor incentive spirometry. The operations of the various methods described herein are not necessarily limited to the order described or shown in the figures, and one of skill in the art will appreciate, upon studying the present disclosure, variations of the order of the operations described herein that are within the spirit and scope of the disclosure. Let it be appreciated that operations of method 300 may be performed multiple times.

The operations and sub-operations of method 300 may be carried out, in some cases, by and/or using one or more of the components, elements, devices, and sub-components of portable monitoring device 200 and/or incentive spirometer 100 (including components thereof as described above), as described with respect to at least FIGS. 1, 2A, 2B, and 3-5, as well as components, elements, devices, and sub-components, depicted therein and/or described with respect thereto.

In such instances, the description of method 300 may or may not refer to a corresponding component and/or element, but regardless of whether an explicit reference is made, one of skill in the art will recognize, upon studying the present disclosure, when the corresponding component and/or element may be used. Further, it will be appreciated that such references do not necessarily limit the described methods to the particular component and/or element referred to. Thus, it will be appreciated by one of skill in the art that aspects and features described above in connection with (sub-) components, elements, devices, and components, including variations thereof, may be applied to the various operations described in connection with method 300 without departing from the scope of the present disclosure.

Referring now to FIG. 3, aspects of the example method 300 for monitoring incentive spirometry are depicted. The portable monitoring device is connected to the incentive spirometer at operation 302. At operation 304, medical personnel may set the desired air volume for a patient. The desired air volume may be set as discussed above with respect to FIGS. 1, 2A, and 2B. The desired air volume may correspond to the predicted goal of the user, and may represent a standardized air volume based on a user's sex, weight, height, age, and/or other parameters specific to an individual, including for example, BMI (i.e., body-mass index), exercise history, smoking history, history of cancer, etc. The desired air volume may be an air volume between the range of about 250 mL to about 3000 mL. A person of ordinary skill in the art would know that the desired air volume may vary within the range based on the specifics of the therapy and the capacity of the incentive spirometer.

In various embodiments, the desired air volume is received from the incrementing of, by example, the first switch 204 and/or the decrementing of the second switch 206 discussed with respect to FIG. 2B. For example, the first switch 204 may increment the desired air volume as follows:

$$V_{ref} = V_{ref} + n(500 \text{ mL}),$$

where $V_{ref}$ is the desired volume amount and n is the number of times the first switch 204 is pressed. In the above example equation, the increments are set at 500 mL. This increment is merely for discussion purposes and embodiments of the technology disclosed herein can have increments of various size, depending on the level of specificity desired. The inverse may be used for the second switch 206, where the desired air volume is set as:

$$V_{ref} = V_{ref} - n(500 \text{ mL}).$$

Although discussed with respect to first switch 204 and second switch 206, this was merely an example of how the desired air volume may be received. In various embodiments, the desired air volume may be received through a different action of one or more switches of the device, as discussed above with respect to FIG. 2A. A person of ordinary skill would not view this recitation of setting the desired air volume as limiting.

In various embodiments, a display of the portable monitoring device (such as display 212 of FIG. 2A, for example) may show the desired air volume to the medical personnel to ensure that it is set correctly. In some embodiments, LEDs or other indicators may be included in the portable monitoring device to indicate whether a desired air volume has been set. For example, a green LED may indicate that the desired air volume is set, while a red or yellow LED may indicate that the desired air volume has not been set yet.

At operation 306, the inspired air volume of the user is captured. A user inhales through the mouthpiece of the incentive spirometer as during regular incentive spirometry. In various embodiments, the inspired air volume may be captured by one or more sensors of the portable monitoring device. The one or more sensors may be configured to determine the inspired air volume through various means, including time of flight of the piston within the air chamber as discussed above. In various embodiments, the inspired air volume may be detected through the use of a light signal, a sound signal, or a combination of both.

At operation 308, the portable monitoring device stores the captured volume of inspired air in a memory or storage component of the portable monitoring device, like the memory 224 of the portable monitoring device 200 discussed with respect to FIG. 2A.

At operation 310, method 300 the portable monitoring device analyzes and processes the data obtained by the one or more sensors. In various embodiments, processing an inspired air volume may include measuring an attempt. An attempt may be registered when the piston 110 reaches (i.e., equals) or exceeds an attempt threshold. An attempt threshold could be a specified air volume that may be between about 0 mL to about 1500 mL. For example, if the attempt threshold is 300 mL; an attempt is registered if the piston reaches or exceeds 300 mL. A person of ordinary skill in the art would know that the specified air volume of the threshold may vary within the range based on the specifics of the therapy and the capacity of the incentive spirometer In embodiments, processing an inspired air volume may include measuring success. A successful attempt may be registered when piston 110 reaches or exceeds the attempt threshold and reaches/exceeds the desired air volume. For example, an attempt threshold may be 250 mL and a desired air volume may be 1500 mL. In this example, a successful attempt will be registered if the piston reaches/exceeds 1500 mL (meaning that the piston had already passed the attempt threshold of 250 mL, registering this as an attempt). It is to be appreciated that more than one attempt may be measured during a session, with a prior attempt being finished when the piston returns to 0 mL and the next attempt beginning when the attempt threshold is reached or exceeded again. In various embodiments, more than one attempt and/or success may be measured over a period of time. In various embodiments, the portable monitoring device may also record failed attempts, failed attempts occurring when the piston reaches or exceeds the attempt threshold but fails to reach the desired inspired air volume.

In various embodiments, processing an inspired air volume at operation 310 may include measuring compliance. In embodiments, compliance is measured by summating the number of successful attempts over a period of time. For example, the number of successful attempts may be 7 and the time elapsed may be 2 hrs; in this example, compliance will be $$\frac{7 * V_{ref}}{2},$$

where $V_{ref}$ is the desired air volume and compliance is measured in mL/hr.

In some embodiments, processing an inspired air volume at operation 310 may include registering a maximum inspired air volume. A maximum inspired air volume (i.e., max volume) refers to highest air volume reached over a period of time. In various embodiments, processing an inspired air volume may include registering a minimum inspired air volume. A minimum inspired air volume (i.e., min volume) refers to the lowest volume reached during a valid attempt (i.e., where the piston has reached or exceeded the attempt threshold) over a period time.

In various embodiments, more than one attempt may be measured over a period of time (t). In embodiments, the period of time (t) may be in units of years, months, weeks, days, hours, minutes, seconds, or any combination thereof.

In some embodiments, processing at operation 310 may include measuring success of an attempted inspiration (an inspired air volume during a period of time). Success (i.e., successful inspiration) may be registered when piston 110 reaches or exceeds the certain threshold and reaches/exceeds the desired air volume. For example, a certain threshold may be 300 mL and a desired air volume may be 1400 mL; a success will be registered if the piston reaches/exceeds 1400 mL. It is to be appreciated that more than one successes may be measured. In various embodiments, more than one success may be measured over a period of time (t). In embodiments, the period of time (t) may be in units of years, months, weeks, days, hours, minutes, seconds, or any combination thereof.

A counter may be incremented when a success is registered during a period of time (t) at operation 310. In various embodiments, the period of time (t) may be in units of years, months, weeks, days, hours, minutes, seconds, or any combination thereof. In some embodiments, operation 310 may include summing the plurality of increments over the period of time (t).

In some embodiments, the following algorithm may be employed:

$$V_{acc} = \Sigma v_{i_c}, c \in [0-p],$$

where $V_{acc}$ is the accumulated inspired air volume, $V_{i_c}$ is the volume of inspired air following each successful attempt c. A time period (t) may have as many as p successful attempts. Thus, each $V_i$ represents the desired air volume set by the user ($V_{ref}$) at a given instant c for discrete events. The accumulated inspired air volume can then be compared with the desired air volume $V_{ref}$ to determine whether a patient as achieved a desire air volume over time, or complied with the recommended therapy.

In various embodiments, the portable monitoring device can measure the inhale/respiratory rate of a patient. The inhale/respiratory rate measured how fast it takes for a single attempt (starting from when the piston reaches the attempt threshold) to reach the desired air volume. For example, the inhale/respiratory rate may be calculated as:

$$RR = \frac{(V_{ref} - V_{threshold})}{t},$$

where RR is the respiratory rate and $V_{threshold}$ if the attempt threshold. The calculated RR can be used to calculate an average respiratory rate ($RR_{avg}$) for the patient over a number of successful attempts, for example $$RR_{avg} = \frac{\sum RR}{\Delta t}.$$

At operation 312, the portable monitoring device can display the results of the processing operation. In some embodiments, the results displayed could include, but is not limited to: attempt(s); success(es); compliance; maximum inspired air volume; and minimum inspired air volume; or a combination thereof.

In various embodiments, operation 312 may include displaying an elapsed time. In embodiments, the elapsed time may be in units of years, months, weeks, days, hours, minutes, or seconds. In embodiments, the elapsed time may be displayed by the display 212. In embodiments, the elapsed time may be displayed by the plurality of LEDs 214.

In various embodiments, operation 312 may include displaying a desired air volume. In embodiments, the desired air volume may be displayed by the display 212. In embodiments, the desired air volume may be displayed by the plurality of LEDs 214.

Figure 4:
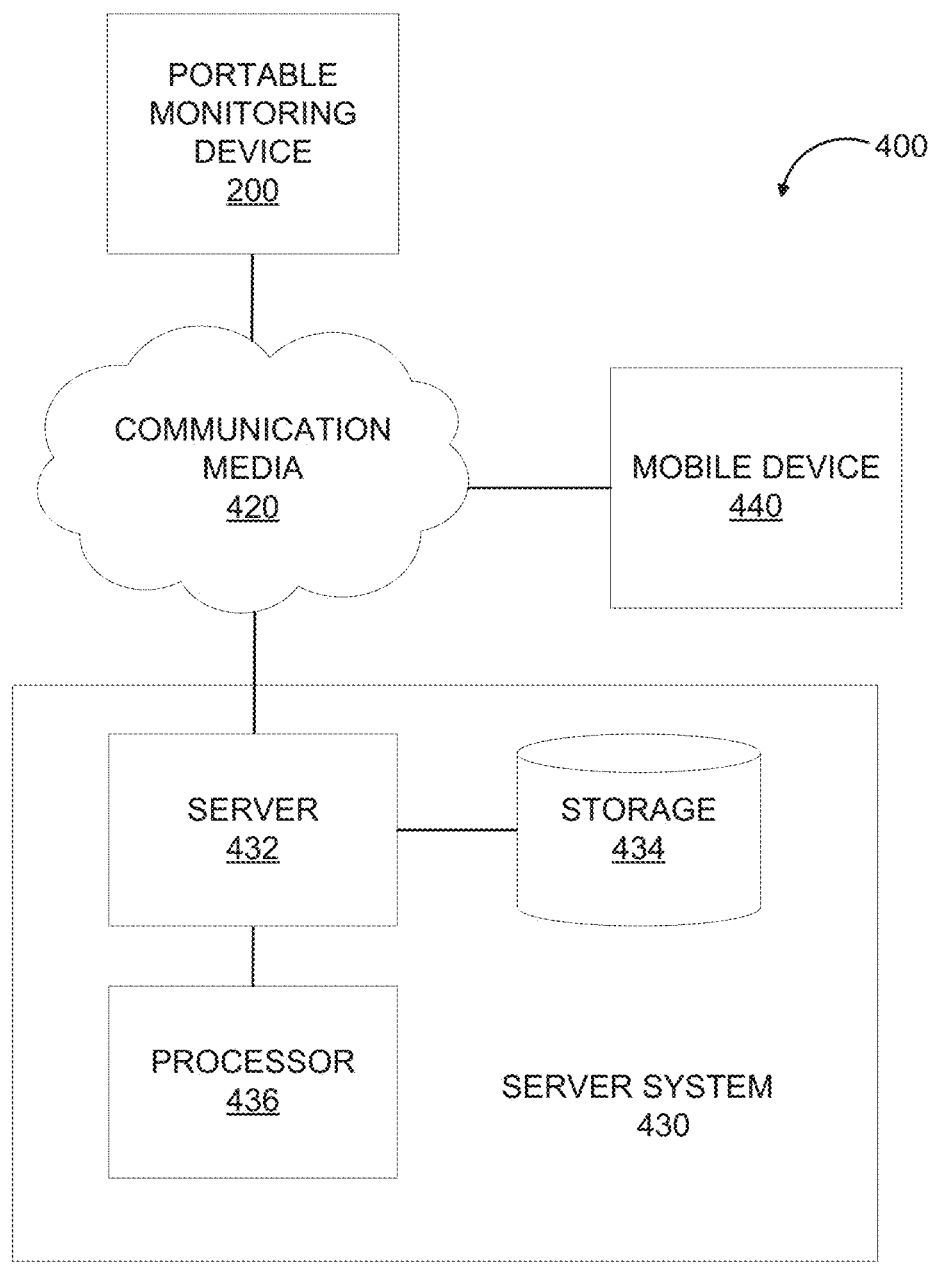
FIG. 4 illustrates an example connection with supplementary computer devices in accordance with embodiments of the disclosure.

There may be a need or want to maintain a record of the data and results obtained through the technology discussed herein. In various embodiments, the portable monitoring device may include an interface to transmit data to a server for storage. FIG. 4 depicts example environment 400, which may be used in connection with implementing embodiments of the disclosed systems, methods, and devices.

As shown in FIG. 4, environment 400 may include one or more of portable monitoring devices 200, one or more mobile devices 440, and server system 430. Portable monitoring device 200 can be coupled to the one or more mobile devices 440 and the server system 430 via communication media 420. As will be described in detail herein, portable monitoring device 200, mobile device 440, and/or server system 430 may exchange communications signals, including information gathered from one or more applications supported by portable monitoring device 200, and other aspects of content for display on portable monitoring device 200 via communication media 420.

Portable monitoring device 200 may communicate with other devices (e.g., mobile device 440) and/or with one another over communication media 420 with or without the use of server system 430. In various embodiments, portable monitoring device 200/or server system 430 may be used to perform various processes described herein and/or may be used to execute various operations described herein with regard to one or more disclosed systems and methods. Upon studying the present disclosure, it will be appreciated that environment 400 may include multiple portable monitoring devices, mobile devices 440, communication media 420, server systems 430, servers 432, processors 436, and/or storage 434. Moreover, interested parties (e.g., medical personnel, family members, etc.) may be able to access the server systems 430 to read data and monitor the patient. For example, a medical personnel (not pictured) may be connected to server system 430 in a similar manner as the portable monitoring device (discussed in greater detail below) using a mobile device 440, enabling the medical personnel to monitor the patient's performance remotely without the need for the patient and medical personnel to be in the same location. Non-limiting examples of mobile device 440 include: smartphones; tablets; laptops; desktops; PDAs; among other portable computing devices.

As mentioned, communication media 420 may be used to connect or communicatively couple portable monitoring device 200 and/or server system 430 to one another or to a network, and communication media 420 may be implemented in a variety of forms. For example, communication media 420 may include an Internet connection, such as a local area network (LAN), a wide area network (WAN), a fiber optic network, internet over power lines, a hard-wired connection (e.g., a bus), and the like, or any other kind of network connection. Communication media 420 may be implemented using any combination of routers, cables, modems, switches, fiber optics, wires, radio (e.g., microwave/RF links), and the like. Further, communication media 420 may be implemented using various wireless standards, such as Bluetooth, Wi-Fi, 3GPP standards (e.g., 2G GSM/GPRS/EDGE, 3G UMTS/CDMA2000, 4G LTE/LTE-U/LTE-A, 5G). Upon reading the present disclosure, one of skill in the art will recognize other ways to implement communication media 420 for communications purposes.

Likewise, though not shown, it will be appreciated that a similar communication medium may be used to connect or communicatively couple server 432, processors 436, and/or storage 434 to one another, in addition to other elements of environment 400. In example embodiments, communication media 420 may be, or include, a wired or wireless wide area network (e.g., cellular, fiber, and/or circuit-switched connection) for portable monitoring device 200 and/or server system 430, which may be relatively geographically disparate; and in some cases, aspects of communication media 420 may involve a wired or wireless local area network (e.g., Wi-Fi, Bluetooth, unlicensed wireless connection, USB, HDMI, and/or standard AV), which may be used to communicatively couple aspects of environment 400 that may be relatively close, geographically. In various embodiments, server system 430 may be co-located with the portable monitoring device (e.g., in the same office, etc.), while in other embodiments the server system 430 may be remotely located (e.g., a data center, cloud system, etc.).

Server system 430 may provide, receive, collect, or monitor information from the portable monitoring device 200, such as, for example, attempts, successes, compliance, elapsed time, desired air volume, minimum inspired air volume, maximum inspired air volume, and the like. Server system 430 may be configured to receive or send such information via communication media 420. This information may be stored in storage 434 and may be processed using processors 436. In some embodiments, some information may be removed from the information gathered, for example, metadata, envelopes, IP addresses, personally identifying information and/or other information. For example, processors 436 may include an analytics engine capable of performing analytics on information that server system 430 has collected, received, or otherwise interacted with, from the portable monitoring device 200. In embodiments, server 432, storage 434, and processors 436 may be implemented as a distributed computing network or as a relational database or the like.

Server 432 may include, for example, an Internet server, a router, a desktop or laptop computer, a smartphone, a tablet, a processor, a component, or the like, and may be implemented in various forms, including, for example, an integrated circuit or collection thereof, a printed circuit board or collection thereof, or in a discrete housing/package/rack or multiple of the same.

In embodiments, server 432 directs communications for portable monitoring device 200 over communication media 420. Server 432 may update information stored on portable monitoring device 200. Server 432 may send/receive information to/from the portable monitoring device 200 in real time or sporadically. Further, server 432 may implement cloud computing capabilities for the portable monitoring device 200.

Figure 5:
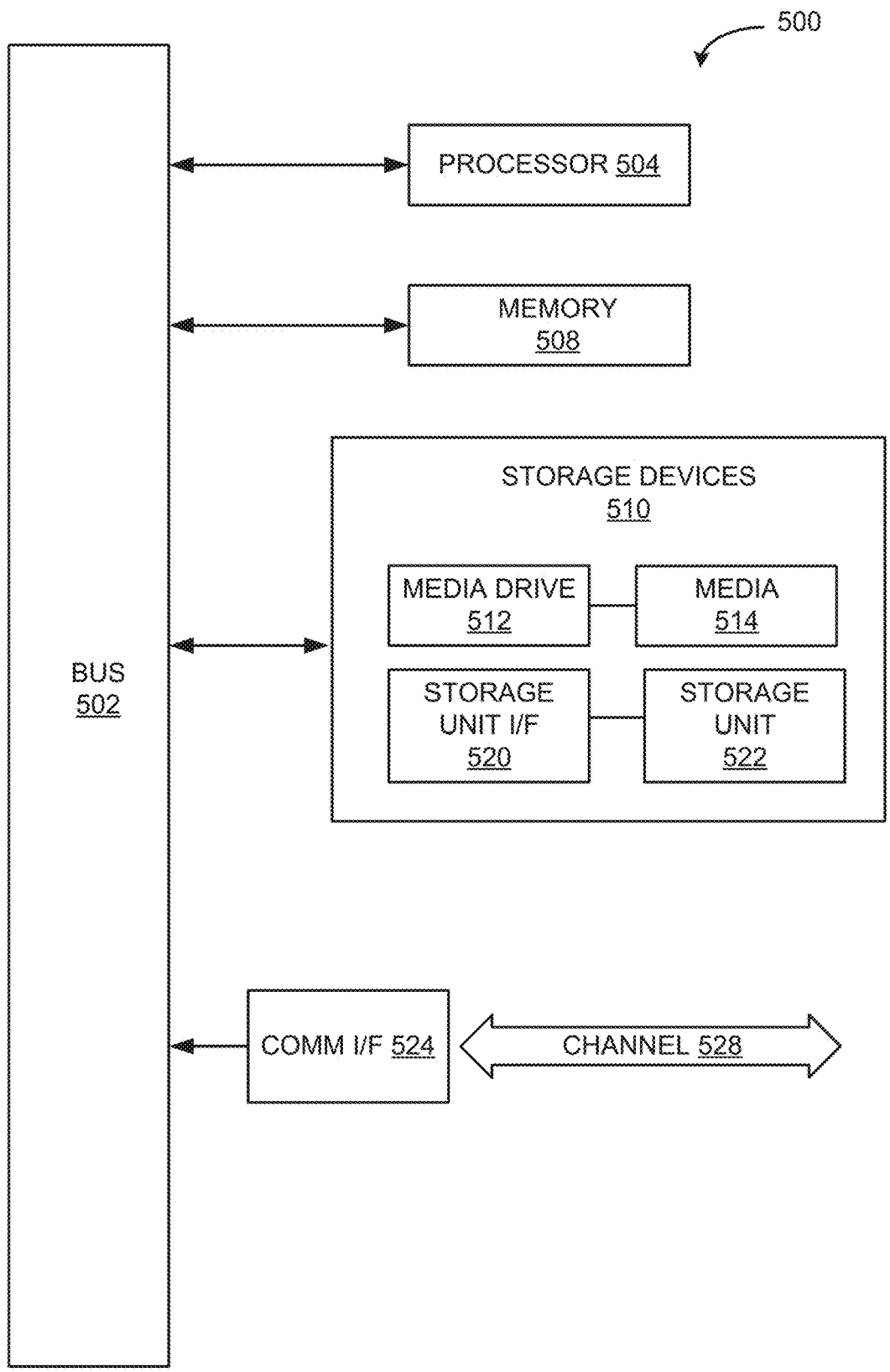
FIG. 5 is an example of a computing component that can be used in conjunction with various embodiments of the present disclosure.

FIG. 5 illustrates example computing component 500, which may in some instances include a processor/controller resident on a computer system (e.g., portable monitoring device 200). Computing component 500 may be used to implement various features and/or functionality of embodiments of the systems, devices, and methods disclosed herein. With regard to the above-described embodiments set forth herein in the context of systems, devices, and methods described with reference to FIGS. 1 through 4, including embodiments involving portable monitoring device 200, one of skill in the art will appreciate additional variations and details regarding the functionality of these embodiments that may be carried out by computing component 500. In this connection, it will also be appreciated by one of skill in the art upon studying the present disclosure that features and aspects of the various embodiments (e.g., systems) described herein may be implemented with respected to other embodiments (e.g., methods) described herein without departing from the spirit of the disclosure.

As used herein, the term component may describe a given unit of functionality that may be performed in accordance with one or more embodiments of the present application. As used herein, a component reference a module, and/or may be implemented utilizing any form of hardware, software, or a combination thereof. For example, one or more processors, controllers, ASICs, PLAs, PALs, CPLDs, FPGAs, logical components, software routines or other mechanisms may be implemented to make up a component. In embodiment, the various components described herein may be implemented as discrete components or the functions and features described may be shared in part or in total among one or more components. In other words, as would be apparent to one of ordinary skill in the art after reading this description, the various features and functionality described herein may be implemented in any given application and may be implemented in one or more separate or shared components in various combinations and permutations. Even though various features or elements of functionality may be individually described or claimed as separate components, one of ordinary skill in the art will understand upon studying the present disclosure that these features and functionality may be shared among one or more common software and hardware elements, and such description shall not require or imply that separate hardware or software components are used to implement such features or functionality.

Where components of the application are implemented in whole or in part using software, in one embodiment, these software elements can be implemented to operate with a computing or processing component capable of carrying out the functionality described with respect thereto. One such example computing component is shown in FIG. 5. Various embodiments are described in terms of this example-computing component 500. After reading this description, it will become apparent to a person skilled in the relevant art how to implement the application using other computing components or architectures.

Referring now to FIG. 5, computing component 500 may represent, for example, computing or processing capabilities found within a self-adjusting display, desktop, laptop, notebook, and tablet computers; hand-held computing devices (tablets, PDA's, smart phones, cell phones, palmtops, etc.); workstations or other devices with displays; servers; or any other type of special-purpose or general-purpose computing devices as may be desirable or appropriate for a given application or environment. Computing component 500 might also represent computing capabilities embedded within or otherwise available to a given device. For example, a computing component might be found in other electronic devices such as, for example navigation systems, portable computing devices, and other electronic devices that might include some form of processing capability.

Computing component 500 might include, for example, one or more processors, controllers, control components, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing component 500 or to communicate externally.

Computing component 500 might also include one or more memory components, simply referred to herein as main memory 508. For example, preferably random access memory (RAM) or other static or dynamic memory, might be used for storing information and instructions to be executed by processor 504. Main memory 508 might also be used for storing temporary variables or other intermediate information during execution of instructions to be executed by processor 504. Computing component 500 might likewise include a read only memory ("ROM") or other static storage device coupled to bus 502 for storing static information and instructions for processor 504.

The computing component 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a solid state drive, a magnetic tape drive, an optical disk drive, a compact disc (CD) or digital video disc (DVD) drive (R or RW), or other removable or fixed media drive might be provided. Accordingly, storage media 514 might include, for example, a hard disk, an integrated circuit assembly, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing component 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory component) and memory slot, a PCMCIA slot and card, and other fixed or removable storage units 522 and interfaces 520 that allow software and data to be transferred from the storage unit 522 to computing component 500.

Computing component 500 might also include a communications interface 524. Communications interface 524 might be used to allow software and data to be transferred between computing component 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 500 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, floor charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The details of some embodiments of the systems and methods of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

The invention claimed is:

1. A portable incentive spirometry monitoring device, comprising:
   a user interface comprising a plurality of switches configured to enable a user to input and set a desired air volume, the desired air volume comprising a goal for a patient to achieve based on a standardized air volume based on one or more patient-specific parameters;
   a sensor measuring inspired air volume in an incentive spirometer when said incentive spirometer is operatively connected to the portable incentive spirometry monitoring device by tracking displacement of a piston within the incentive spirometer;

a processor configured to:

increment a counter each time the piston is displaced up to or exceeding the desired air volume input;

determine compliance by a patient inspiring air using the incentive spirometer based on a summation of successes of a period of time, a success indicated by a value of the counter;

a display presenting a visual indication of the number of times the piston has been displaced up to or exceeding the desired air volume input; and a plurality of connectors disposed on a top of the portable incentive spirometry monitoring device configured to mate with a base of the incentive spirometer.

2. The portable incentive spirometry monitoring device of claim 1, wherein the sensor measures the inspired air volume by tracking a time of flight of the piston through a light signal.

3. The portable incentive spirometry monitoring device of claim 1, wherein the sensor measures the inspired air volume by tracking the time of flight of the piston through a sound signal.

4. The portable incentive spirometry monitoring device of claim 1, wherein the display presents a plurality of parameters including at least one of a number of attempts, a number of successes, a goal, an elapsed time, a maximum volume, and a minimum volume.

5. The portable incentive spirometry monitoring device of claim 1, wherein the display is an LCD screen.

6. The portable incentive spirometry monitoring device of claim 1, wherein the display is a plurality of LEDs.

7. The portable incentive spirometry monitoring device of claim 1, wherein the portable incentive spirometry monitoring device is operationally attached to the incentive spirometer.

8. The portable incentive spirometry monitoring device of claim 1, wherein the portable incentive spirometry monitoring device is operationally detached from the incentive spirometer.

* * * * *